US012582697B2

(12) United States Patent
Larsson

(10) Patent No.: US 12,582,697 B2
(45) Date of Patent: Mar. 24, 2026

(54) ANTISECRETORY FACTOR FOR USE IN TREATMENT AND/OR PREVENTION OF ACUTE RESPIRATORY FAILURE

(71) Applicant: LANTMÄNNEN MEDICAL AB, Stockholm (SE)

(72) Inventor: Anders Larsson, Stockholm (SE)

(73) Assignee: LANTMÄNNEN MEDICAL AB, Stockholm (SE)

( * ) Notice: Subject to any disclaimer, the term of this patent is extended or adjusted under 35 U.S.C. 154(b) by 375 days.

(21) Appl. No.: 16/973,985

(22) PCT Filed: Jun. 26, 2019

(86) PCT No.: PCT/EP2019/067067
§ 371 (c)(1),
(2) Date: Dec. 10, 2020

(87) PCT Pub. No.: WO2020/002464
PCT Pub. Date: Jan. 2, 2020

(65) Prior Publication Data
US 2025/0177480 A1 Jun. 5, 2025

(30) Foreign Application Priority Data

Jun. 28, 2018 (SE) .................................... 1850803-6

(51) Int. Cl.
*A61K 38/17* (2006.01)
*A61P 11/00* (2006.01)

(52) U.S. Cl.
CPC .......... *A61K 38/1709* (2013.01); *A61P 11/00* (2018.01)

(58) Field of Classification Search
None
See application file for complete search history.

(56) References Cited

FOREIGN PATENT DOCUMENTS

| WO | WO97/08202 A1 | 3/1997 |
| WO | WO98/21978 A1 | 5/1998 |
| WO | WO00/38535 A1 | 7/2000 |
| WO | WO2005/030246 A1 | 4/2005 |
| WO | WO2007/126363 A2 | 11/2007 |
| WO | WO2007/126364 A2 | 11/2007 |
| WO | WO2007/126365 A2 | 11/2007 |
| WO | WO2010/093324 A1 | 8/2010 |
| WO | WO2017/009004 A1 | 1/2017 |
| WO | WO2018/015379 A1 | 1/2018 |

OTHER PUBLICATIONS

Nicolas V and Moal V "Antisecretory Factor Peptide AF-16 Inhibits the Secreted Autotransporter Toxin-Stimulated Transcellular and Paracellular Passages of Fluid in Cultured Human Enterocyte-Like Cells" Infect Immun 83:907-922. (Year: 2015).*
Wong et al. "Machine Learning Methods to Predict Acute Respiratory Failure and Acute Respiratory Distress Syndrome" Front. Big Data 3:579774. (Year: 2020).*
Ulgheri, C., et al., "Antisecretory factor as a potential health-promoting molecule in man and animals," Nutr. Res. Rev. 2010;23:300-313.
International Search Report and Written Opinion for PCT Patent App. No. PCT/EP2019/067067 (Oct. 2, 2019).
Lange, S., et al., "The Antisecretory Factor: Synthesis, Anatomical and Cellular Distribution, and Biological Action in Experimental and Clinical Studies," Int. Rev. Cytol. 2001;210:39-75.
Hansson, H.-A., et al., "The Peptide AF-16 and the AF Protein Counteract Intracranial Hypertension," Acta Neurochir. Suppl. 2012;114:377-382.
Altschul, S. F., et al., "Basic Local Alignment Search Tool," J. Mol. Biol. 1990;215:403-410.
Calfee, C. S., et al., "Trauma-associated lung injury differs clinically and biologically from acute lung injury due to other clinical disorders," Crit. Care Med. 2007;35(10):2243-2250.
Claesson, J., et al., "Scandinavian clinical practice guideline on fluid and drug therapy in adults with acute respiratory distress syndrome," Acta Anaesth. Scand. 2016;60:697-709.
Huppert, L. A., et al., "Alveolar Fluid Clearance in Pathologically Relevant Conditions: In Vitro and In Vivo Models of Acute Respiratory Distress Syndrome," Front. Immunol. 2017;8(371):6 pp.
"Remington: The science and practice of pharmacy," 21st Edition, ISBN 0-7817-4673-6 or "Encyclopedia of pharmaceutical technology," 2nd edition, ed. Swarbrick J., ISBN: 0-8247-2152-7, 2005, Lippincott Williams & Wilkins, Baltimore, MD, US, 14 pp.
Sakka, S. G., "Extravascular lung water in ARDS patients," Minvera Anestesiol. 2013;79:274-284.

(Continued)

*Primary Examiner* — Sudhakar Katakam
*Assistant Examiner* — Zachary J Miknis
(74) *Attorney, Agent, or Firm* — Cermak & McGowan LLP; Malcolm K. McGowan

(57) ABSTRACT

The present invention relates to the use of antisecretory factor (AF) protein, homologues, and/or fragments thereof, having equivalent functional activity, and/or a pharmaceutically active salt thereof, for restoring and/or normalizing epithelial barrier function for treating and/or preventing acute respiratory failure.

Figure 1:
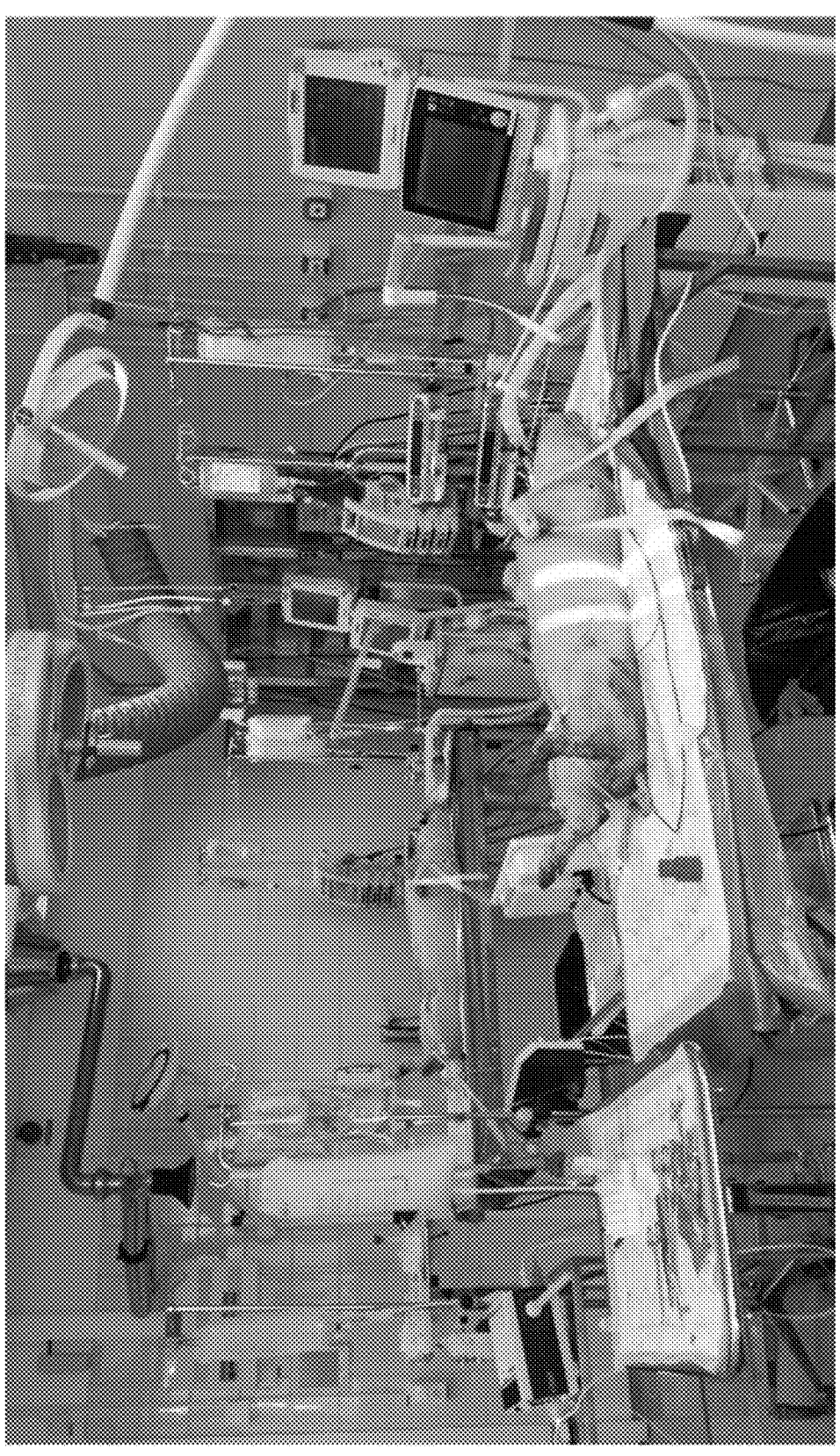

In particular, antisecretory factor (AF) protein, homologues, and/or fragments thereof, having equivalent functional activity, and/or a pharmaceutically active salt thereof, is (are) herein disclosed to be of use in counteracting and/or normalizing fluid transfer across epithelial cell barriers with a significant impact on a large proportion of patients with traumatic lung injury, such as but not limited to patients suffering from abnormal accumulation of fluid in the lung alveoli and/or bronchioles selected from the list of patients suffering from BPD, ARDS, IRDS, sepsis, SIRS, acute pulmonary edema, pneumonia, interstitial pulmonary edema and cardiovascular lung disorder.

12 Claims, 4 Drawing Sheets

Specification includes a Sequence Listing.

(56)        References Cited

OTHER PUBLICATIONS

Singer, M., et al., "The Third International Consensus Definitions for Sepsis and Septic Shock (Sepsis-3)," JAMA 2016;315:801-810.
Lange, S., et al., "The antisecretory factor: synthesis and intracellular localisation in porcine tissues," Cell Tissue Res. 1999;296:607-617.
Scala, R., et al., "Highlights in acute respiratory failure," Eur. Respir. Rev. 2018;27:4 pp.
International-Type Search Report, Search Request No. ITS/SE18/00026, Jan. 30, 2019.

* cited by examiner

ANTISECRETORY FACTOR FOR USE IN TREATMENT AND/OR PREVENTION OF ACUTE RESPIRATORY FAILURE

CROSS-REFERENCE TO RELATED APPLICATIONS

The present application is a continuation of PCT/EP2019/067067, filed Jun. 26, 2019, which claims priority from Swedish patent application 1850803-6, filed Jun. 28, 2018. The contents of these priority applications are incorporated herein by reference in their entirety.

FIELD OF INVENTION

The present invention relates to the use of an antisecretory factor protein (AF), a homologue, and/or fragment thereof, having equivalent functional activity, and/or a pharmaceutically active salt thereof, for restoring and/or normalizing epithelial barrier function in pathogenesis of acute respiratory failure (ARF).

In particular, an antisecretory factor (AF) protein, a homologue, and/or fragment thereof, having equivalent functional activity, and/or a pharmaceutically active salt thereof, is (are) herein disclosed to be of use in counteracting and/or normalizing fluid transfer across epithelial barriers with a significant impact on a large proportion of patients with acute respiratory failure, such as patients with abnormal accumulation of fluid in the lung alveoli and bronchioles due to acute respiratory failure (ARF) including but not limited to: ARDS (acute respiratory distress syndrome), and IRDS (infant respiratory distress syndrome).

BACKGROUND OF THE INVENTION

Epithelial Barriers

The lining of surfaces within and on a body, such as the skin, as well as the respiratory tract, the lungs, and the mucosal membranes of the gastrointestinal and urinary tract, are an important line of defense, preventing e.g. the invasion of microorganisms and their products as well as abnormal flow and/or distribution of fluid and solutes.

Epithelial cells establish a barrier between normally hostile external environments and the internal milieu. However, cell linings are also responsible for fluid, solute and nutrient absorption and secretion of a wide range of products including waste and activities that require a selectively permeable barrier. These functions place the epithelium at the center of interactions between e. g. the mucosal immune system and luminal contents, including dietary antigens and microbial products, as well as enclosing cells and their interstitial fluid.

Immune competent cells, especially lymphocytes, are involved in maintaining the integrity of these epithelial barriers. They contribute towards the tolerance to commensal organisms, which occupy these same sites, and to the immune responses against harmful organisms and their products.

The concept "epithelial barrier" is a generic term of a diverse group of epithelial cells, which cover or line all body surfaces, cavities and tubes. This may be illustrated by the epithelial cells outlining blood and lymph vessels, which are named endothelial cell. Epithelial cells are firmly attached to underlying tissues and organs by a basement membrane. Epithelial cells mediate a wide range of activities such as selective diffusion, uptake, absorption, secretion, physical protection and containment. A very important function of epithelial barriers is selective, precise separation of lumens, as well as control of e.g. the composition of the fluid and solutes separated from air.

Epithelial barrier function requires a continuous layer of cells as well as junctions that seal the paracellular space between epithelial cells. Along with plasma membranes, the intercellular tight junction is the primary cellular determinant of epithelial barrier function. Disruption of tight junction structures, as a result of specific protein mutations or aberrant regulatory signals, can be both a cause and an effect of disease.

In the lungs, airway epithelial cells form a barrier to the air/gas in the outside world and are at the front line of mucosal immunity. Epithelial apical junctional complexes are formed by a range of protein subunits that promote cell-cell adhesion and barrier integrity. The integrity of the airway epithelium in patients with e. g. asthma or bronchitis is often disrupted, with variable loss of epithelial cell-cell contacts. Repair events may result in the formation of undifferentiated, disturbed and dysfunctional cells. Further, damage to the barrier functions of the airway epithelium enhances mucosal permeability of foreign substances through the airway epithelium. Thus, it is suggested that airway epithelial barrier dysfunction may have important implications for e.g. asthma, because structural epithelial barrier function is interwoven with the ability of the epithelium to regulate the immune system and to be regulated by it.

Compromised epithelial cell barrier function has thus been associated with a number of disease states, e.g. intestinal, pulmonary, cardiovascular and systemic. Unfortunately, most current clinical data are correlative, making it difficult to separate cause from effect in interpreting the importance of barrier loss. No FDA-approved agents that target the epithelial barrier to repair, restore and tune it, are presently available. To develop such therapies, a deeper understanding of both disease pathogenesis and mechanisms of barrier regulation must be reached.

Acute Respiratory Failure (ARF)

The term "acute respiratory failure (ARF)" is in the present context used interchangeably with "acute lung injury", "traumatic lung injury" and "trauma-associated lung injury", and encompasses acute respiratory distress syndrome (ARDS), which is divided in mild, moderate and severe, depending of the severity of the condition. ARDS results from a systemic illness and/or injury to lung cells, such as, but not limited to, a trauma. The latter may be due to pneumonia, inhalation of toxic substances, accidents such as falls, traffic accident or penetrating trauma, mechanical ventilation, immunological reactions, cardiovascular dysfunction or sepsis. Brain damage due to hemorrhages, stroke and trauma are additional causes. ARDS is associated with a reduced alveolar liquid clearance (ALC) capacity, a disruption of the alveolar epithelial barrier, and an increased capillary endothelial permeability, resulting in increasing alveolar and bronchiolar fluid accumulation.

According to a previous study, it is alleged that the pathophysiology, as a result of trauma related to acute lung injuries, may be different than the ones arising from a non-trauma induced lung injury. Trauma patients have significantly lower plasma levels of biomarkers of lung epithelial and endothelial injury, previously found to be prognostic in acute lung injury. The conclusion is that trauma patients tend to have on average less severe lung epithelial and endothelial injury than patients with other clinical risks for lung injury (see Calfee et al. 2007). Hence, it would be beneficial to gain an increased possibility for restoring and/or normalizing the epithelial barrier function in traumatic lung injured patients having had their lungs injured, irrespective of damage mechanism.

In addition, ARF can also be due to sepsis, other severe systemic inflammatory conditions and/or cardiovascular lung and/or brain disorders. Consequently, the present invention also relates to the use of antisecretory factor (AF) protein, homologues, and/or fragments thereof, having equivalent functional activity, and/or a pharmaceutically active salt thereof, for restoring and/or normalizing epithelial barrier function in pathogenesis of acute respiratory failure (ARF) in patients suffering from sepsis, systemic inflammatory conditions and/or cardiovascular lung and/or brain disorders.

In addition, staying at a high altitude may as well induce acute lung damage, as does drowning.

Acute Respiratory Distress Syndrome (ARDS)

ARDS is characterized by a non-cardiogenic dyspnea, tachypnea, accumulation of fluid in the lungs' alveoli, bilateral chest radiograph opacities and hypoxemia refractory to oxygen therapy. It ought to be stressed that about one third of the ARDS patients at early disease stages do not have any demonstrable extra fluid in their alveoli although the alveolar cell lining is damaged (Sakka 2013; Claesson et al., 2016; Huppert and Matthay, 2017). I ARDS is a common cause of admission to the ICU (intensive care units) at hospitals due to hypoxemic respiratory failure, a serious condition often requiring mechanical ventilation.

Corticosteroids are with few exceptions not recommended for ARDS patients. Rescue therapies alleviate hypoxemia in patients unable to maintain reasonable oxygenation: recruitment maneuvers, prone positioning, inhaled nitric oxide, high-frequency oscillatory ventilation, and extracorporeal membrane oxygenation improve oxygenation, but their impact on mortality, with the exception of prone positioning, remains unproven. Restrictive fluid management to avoid deleterious overload of fluid in the lungs seems to be a favorable strategy but with no significant reduction in 60-day mortality.

Cardiogenic overload of the lungs by blood and fluid may result in deleterious, life-threatening conditions simulating ARDS.

Infant Respiratory Distress Syndrome

IRDS (infant respiratory distress syndrome) is a syndrome in premature infants caused by insufficient production of pulmonary surfactant and not fully developed structure of the immature lungs.

Bronchopulmonary Dysplasia (BPD)

Bronchopulmonary dysplasia (BPD) is a form of chronic lung disease that affects newborns, in particular prematurely born babies, and infants. It results from damage to the lungs caused by mechanical ventilation such as, but not limited to respirators, and long-term use of oxygen. Most infants recover from BPD, but some may have long-term breathing difficulty.

ARF includes BPD, IRDS and ARDS and is characterized by damage of the capillary epithelium and alveolar epithelium in association with impaired fluid removal from alveolar space and the accumulation of protein-rich fluid inside the alveoli. Concomitantly, alveolar cells form and release inflammation promoting substances, adding to the acute lung disorder. Thus, the injured patients suffer from an impaired epithelial barrier generating an increased capillary permeability, hampering the lung function, the oxygenation and impair the systemic functions of the body's organs and cardiovascular systems.

Acute lung injuries, in particular ARDS and similar disorders, exert a substantial disease burden, with about 40% of patients dying in hospital in spite of advanced modern medico-technically treatment (Claesson et al., 2016; Huppert and Matthay, 2017). Diverse factors, including patient-related factors such as age and illness severity, country level, socioeconomic status, ventilator management and ICU organizational factors each contribute to the outcome from these lung injuries. Only a few treatment strategies have been shown to improve survival outcomes.

The Antisecretory Factor (AF) Protein

Antisecretory factor (AF) is a 41 kDa protein that was originally described to provide protection against diarrhea diseases and intestinal inflammation (for a review, see Lange and Lönnroth, 2001). The antisecretory factor (AF) protein has long since been sequenced and its cDNA cloned. The antisecretory activity seems to be mainly exerted by a peptide located between the amino acid positions 35 and 50 on the antisecretory factor (AF) protein sequence which comprises at least 4-16, such as 4, 5, 6, 7, 8 or 16 amino acids of the consensus sequence. Immunochemical and immunohistochemical investigations have revealed that the antisecretory factor (AF) protein is present and may also be synthesized by most tissues and organs in a body. Synthetic peptides, comprising the antidiarrheal sequence, i.e. at least the amino acid sequence shown in SEQ.ID.NO: 2 which is located in the consensus sequence, have prior been characterized (WO 97/08202; WO 05/030246; WO 2007/126364; WO 2018/015379).

Antisecretory factor (AF) proteins and peptides have previously been disclosed to normalize pathological fluid transport and/or inflammatory reactions, such as in the intestine and in the central nervous system after challenge with a cholera toxin (WO 97/08202). Food and feed with the capacity to either induce endogenous synthesis of AF or uptake of added AF have therefore been suggested to be useful for the treatment of edema, diarrhea, dehydration and inflammation in WO 97/08202. WO 98/21978 discloses the use of products having enzymatic activity for the production of a food that induces the endogenous formation of antisecretory factor (AF) proteins. WO 00/038535 further discloses food products enriched and/or naturally rich in native antisecretory factor (AF) proteins (NASPs) as such.

Antisecretory factor (AF) proteins and fragments thereof have also been shown to improve the repair of nervous tissue, and proliferation, apoptosis, differentiation, and/or migration of stem and progenitor cells and cells derived thereof in the treatment of conditions associated with loss and/or gain of cells (WO 05/030246) and to be equally effective in the treatment and/or prevention of intraocular hypertension (WO 07/126364), as for the treatment and/or prevention of compartment syndrome (WO 07/126363).

The present inventors have also shown that AF is able to monitor and/or beneficially affect the structure, distribution and multiple functions of lipid rafts, receptors and/or caveolae in membranes and that AF can thus be employed for the treatment and/or prevention of structural disorganization and dysfunction of lipid rafts and/or caveolae in cell membranes (WO 07/126365).

The present inventors have further been able to prove that the same antisecretory factor (AF) protein, peptides and fragments thereof can intervene in the biological activation of transmembrane protein ion channels, e.g. NKCC1 through FAK and CAP, and that they can thus directly regulate the pathological activity of the ion channel in pathological and/or perturbed cells, effectively normalizing the intracellular pressure and transmembrane protein function in said cell, and thus allowing an improved uptake of drugs used in e.g. cancer therapy (WO 2010/093324).

Furthermore, in WO 2014/096384, antisecretory factor (AF) proteins, peptides, homologues and/or fragments thereof were shown to be useful in symptomatic, curative and palliative therapies for glioblastoma.

The present invention relates to the surprising insight that antisecretory factor (AF) also restores and/or normalizes epithelial barrier function in pathogenesis of acute respiratory failure (ARF), thereby e.g. significantly counteracting the accumulation of fluid in the respiratory system and at the same time exerting beneficial effects on the cardiovascular system.

SUMMARY OF THE PRESENT INVENTION

The present application for the first time discloses an antisecretory factor (AF) protein as shown in SEQ ID NO: 1 (AF) and/or a homologue and/or fragment thereof having equivalent activity and comprising an amino acid sequence as shown in SEQ ID NO: 2 (AF-6), and/or a pharmaceutically active salt thereof, and/or a food and/or food supplement, enriched and/or naturally rich in said antisecretory factor (AF) protein and/or homologue and/or fragment thereof, for use in restoring and/or normalizing epithelial and/or endothelial barrier function for treatment, amelioration and/or prevention of acute respiratory failure (ARF).

ARF to be treated, ameliorated and/or prevented is in the present context selected from the group consisting of IRDS, BPD, ARDS, acute pulmonary edema and interstitial pulmonary edema.

The present invention thus relates to the use of an antisecretory factor (AF) protein as shown in SEQ ID NO: 1 (AF) and/or a homologue and/or fragment thereof comprising an amino acid sequence as shown in SEQ ID NO: 2 (AF-6), and/or a pharmaceutically active salt thereof, and/or a food and/or food supplement, enriched and/or naturally rich in said antisecretory factor (AF) protein and/or homologue and/or fragment thereof, for manufacturing a pharmaceutical composition for use in restoring and/or normalizing epithelial barrier function for treating and/or preventing acute respiratory failure.

The invention relates to an antisecretory factor (AF) protein and/or homologue and/or fragment thereof and/or a food and/or food supplement, enriched and/or naturally rich in said antisecretory factor (AF) protein and/or homologue and/or fragment thereof, for use in restoring and/or normalizing epithelial barrier function, wherein epithelial cell barrier functions are restored and/or normalized in patients suffering from acute respiratory failure.

An antisecretory factor (AF) protein and/or a homologue and/or fragment thereof and/or a pharmaceutically active salt thereof, for use according to the present invention can be formulated in a pharmaceutical composition comprising either one or comprising at least two or more antisecretory factor (AF) proteins and/or homologues and/or fragments thereof and/or pharmaceutically active salts thereof. Typically, said pharmaceutical composition further comprises a pharmaceutically acceptable excipient.

The present invention further also relates to said pharmaceutical composition comprising at least one antisecretory factor (AF) protein as shown in SEQ ID NO: 1 (AF) and/or a homologue and/or fragment thereof comprising an amino acid sequence as shown in SEQ ID NO: 2 (AF-6), and/or a pharmaceutically active salt thereof for use in restoring and/or normalizing epithelial barrier function in the pathogenesis of acute respiratory failure.

Furthermore, an antisecretory factor (AF) protein and/or a homologue and/or fragment thereof and/or a pharmaceutically active salt thereof, for use according to the present invention can be formulated as a food and/or food supplement, enriched and/or naturally rich in in said antisecretory factor (AF) protein and/or homologue and/or fragment thereof.

An antisecretory factor (AF) protein and/or a homologue and/or fragment thereof and/or a pharmaceutically active salt thereof, and/or a food and/or food supplement, enriched in said antisecretory factor (AF) protein and/or homologue and/or fragment thereof for use according to the present invention can be formulated for intravascular infusion or injection, for intraocular, intranasal, oral, local, cutaneous, subcutaneous and/or systemic administration, for administration as a spray, aerosol, inhaler and/or by a nebulizer. It can be formulated for administration systemically to the blood at a dose of 0.1 µg to 100 mg per application and kg body weight, preferably at a dose of 1-10000 µg per application and kg body weight. Said administration can be performed either as a single dose, multiple dose and/or as multiple daily applications.

An antisecretory factor (AF) protein and/or a homologue and/or fragment thereof and/or a pharmaceutically active salt thereof, and/or a food and/or food supplement, enriched in said antisecretory factor (AF) protein and/or homologue and/or fragment thereof for use according to the present invention can be provided as egg yolk enriched and/or naturally rich in antisecretory factors, such as egg yolk enriched in and/or with a high natural content of naturally occurring antisecretory factors (NASPs), or as egg yolk with at least 0.05 ng/ml antisecretory factor (AF) protein fragment with an amino acid sequence as disclosed in SEQ ID NO: 3 (AF-16) and/or in SEQ ID NO: 4 (AF-8). Said egg yolk can be spray-dried.

In one embodiment, a method is disclosed for restoring and/or normalizing epithelial barrier function for treatment and/or prevention of ARF, wherein an antisecretory factor (AF) protein as shown in SEQ ID NO: 1 (AF) and/or a homologue and/or fragment thereof comprising an amino acid sequence as shown in SEQ ID NO: 2 (AF-6), and/or a pharmaceutically active salt thereof, a pharmaceutical composition comprising said antisecretory factor (AF) protein as shown in SEQ ID NO: 1 (AF) and/or a homologue and/or fragment thereof comprising an amino acid sequence as shown in SEQ ID NO: 2 (AF-6), and/or a pharmaceutically active salt thereof, and/or a food and/or food supplement, enriched and/or naturally rich in said antisecretory factor (AF) protein and/or homologue and/or fragment thereof, is administered to a mammal in need thereof. Said mammal can be a human.

In consequence, the present invention relates to a method for treatment, amelioration prevention and/or prophylactic treatment of acute respiratory failure, such as for treating and/or preventing ARF, selected from the group consisting of IRDS, BPD, ARDS, acute ARDS, severe ARDS, acute pulmonary edema and interstitial pulmonary edema, wherein a sufficient amount of an antisecretory factor (AF) protein as shown in SEQ ID NO: 1 (AF) and/or a homologue and/or fragment thereof comprising an amino acid sequence as shown in SEQ ID NO: 2 (AF-6), and/or a pharmaceutically active salt thereof, a pharmaceutical composition comprising said antisecretory factor (AF) protein as shown in SEQ ID NO: 1 (AF) and/or a homologue and/or fragment thereof comprising an amino acid sequence as shown in SEQ ID NO: 2 (AF-6), and/or a pharmaceutically active salt thereof, and/or a food and/or food supplement, enriched and/or naturally rich in said antisecretory factor (AF) protein and/or homologue and/or fragment thereof, is administered to a mammal in need thereof. Said mammal can be a human.

FIGURE LEGENDS

FIG. 1: The set up in the laboratory during the experiments. Two deeply anesthetized pigs have each a tracheostomy and are connected to respirator. Two identical sets of intensive care surveillance equipment are further seen. The treatment of either animal was blinded for the attending researchers and the code was not made available until all experiments were done. The core body temperature was checked and kept at 38-39° C.

Figure 2A:
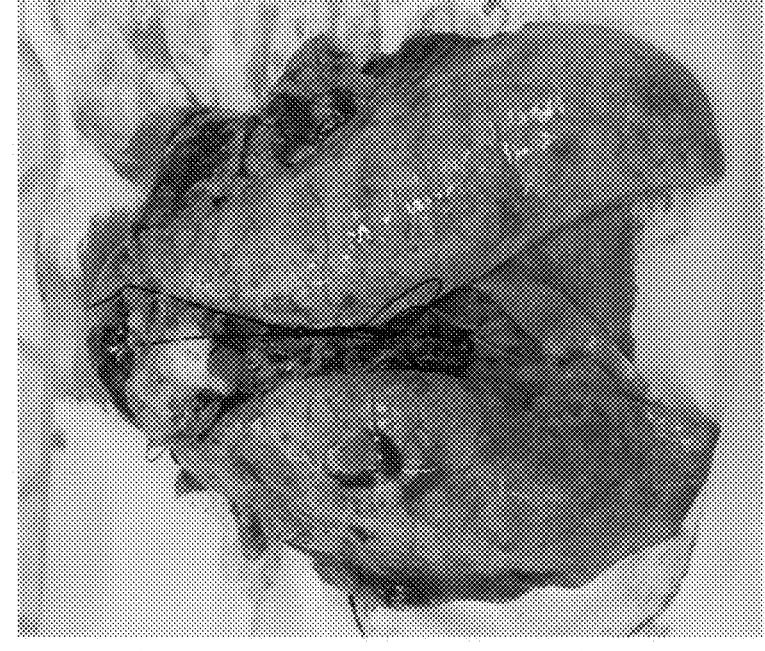
Figure 2B:

FIG. 2: Photos of lungs at 5 hours after injury and 4 hours after either treatment. The left photo (FIG. 2B) illustrates an injured lung treated with the vehicle while in contrast the right lung (FIG. 2A) is from a pig having had 2 mg/kg bw (body weight) AF-16. The left photo (FIG. 2B) discloses that the ALI followed after 1 h by vehicle infusion resulted in the formation of extensive atelectasis and hemorrhages discoloring the lung tissue, appearing dark. Only limited areas of the upper parts of the vehicle treated lungs are of normal appearance, revealing restricted functional capacity of the vehicle lungs. In contrast, the right photo (FIG. 2A) demonstrates that both the left and right lung lobes appear close to normal with minor scattered hemorrhages, illustrating the protective effects of the AF-16 infusion. The efficiency of the AF-16 treatment is strikingly illustrated by the discolored marks on the lungs from a vehicle treated (left) pig related to the increased content of EVLW that forced the pig lungs against the thoracic rib cage.

Figure 3:
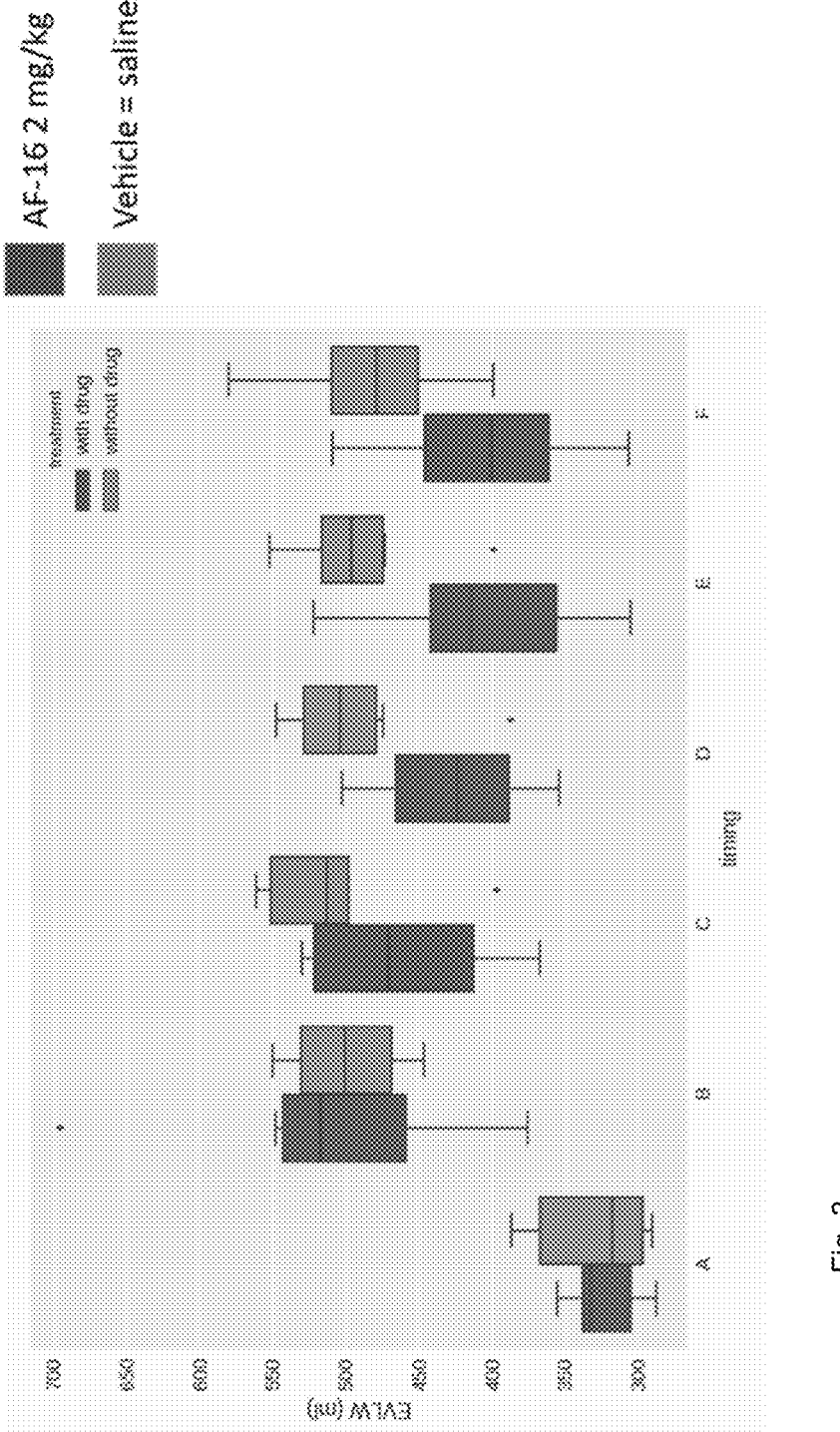

FIG. 3: A key result was the demonstration of the dynamics of the increase in the accumulation of Extra Vascular Lung Water (EVLW) in pigs exposed to lung injury at different timings (A-F). The recorded values are plotted for treatment at one-hour (hourly) intervals, as disclosed by the graph. The time line is related to the treatment:

A: Baseline prior to lung injury with animals prepared for the experiment;
B: 1 h after lung injury and just prior to AF-16/vehicle infusion;
C: 1 h after AF-16/vehicle infusion;
D: 2 h after AF-16/vehicle infusion;
E: 3 h after AF-16/vehicle infusion;
F: 4 h after AF-16/vehicle infusion;

The EVLW fraction increased from about 320 mL at baseline within 1 hour after the lung injury to about 500 mL for either group. The EVLW remained at that level for additionally 4 hours if the pig was treated with the vehicle, saline. In contrast, the EVLW was significantly reduced by treatment with AF-16 after exposure to repeated lung lavage and injurious ventilation from about 500 mL to 400 mL in 4 h, a highly significant ($p<0.001$) and beneficial effect, disclosing a roughly 20% reduction. Such a difference of 100 mL is functionally very beneficial and could be of critical importance, reducing the amount of fluid filled lung regions and improving blood oxygenation. The EVLW was determined with the PiCCO method in 6 pigs with ARDS and having 2 mg/kg bw (bodyweight) AF-16 infused, while 6 ARDS pigs had only the vehicle infused. Treatment coded for the acting researchers.

Figure 4:
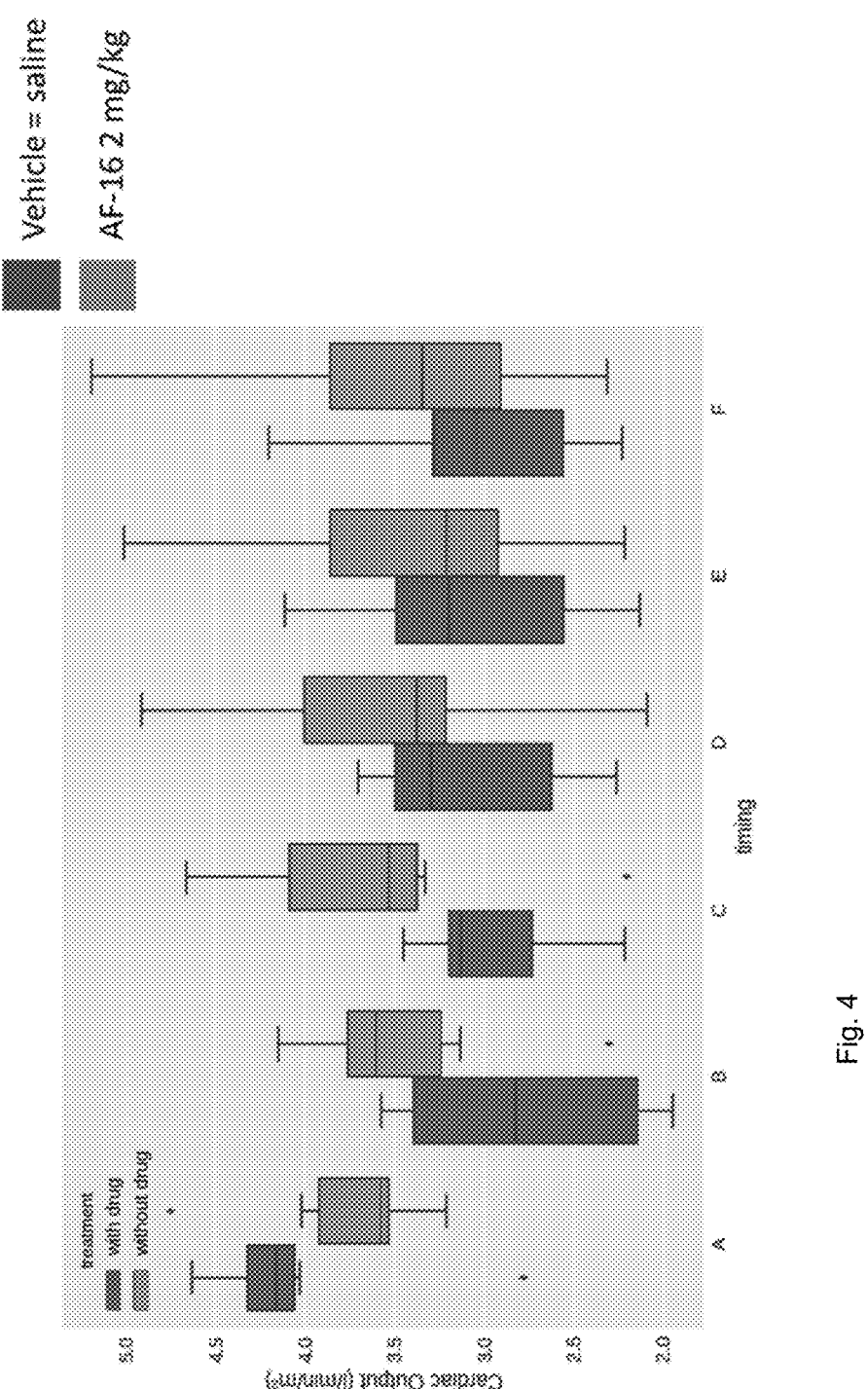

FIG. 4: The heart is structurally and functionally closely associated with the lungs. Impaired lung function is associated with reduced cardiovascular function as disclosed by reduced cardiac output (CO), a sensitive and accurate measure of the functional level of the heart. The graph in FIG. 4 reveals that the induced ALI hamper the CO in the vehicle treated 6 pigs with about 1 L/min/m² from baseline 4.2 L/min/m², corresponding to a decrease of roughly 25% persisting for the next 4 h. In contrast, infusion of 2 mg/kg AF-16 to 6 pigs at 1 h after the ALI kept the CO at a close to normal level, of key importance at such a severe disease as ARDS, clinically considered as highly relevant. The AF-16 infusion significantly ($p<0.05$) increased the CO as compared to that recorded for the vehicle treated animals, and the beneficial effect lasted at least 4 h. Treatment coded for the acting researchers.

DEFINITIONS AND ABBREVIATIONS

Abbreviations

IFP: interstitial fluid pressure;
PBS: phosphate buffered saline;
AF: antisecretory factor,
Full-length AF protein (as shown in SEQ ID NO: 1)
AF-6: a hexa peptide composed of the amino acids CHSKTR (as shown in SEQ ID NO: 2);
AF-16: a peptide composed of the amino acids VCHSKTRSNPENNVGL (as shown in SEQ ID NO: 3);
AF-8: a septa peptide composed of the amino acids VCHSKTR (as shown in SEQ ID NO: 4);
Octa peptide IVCHSKTR (as shown in SEQ ID NO: 5);
Penta peptide HSKTR (as shown in SEQ ID NO: 6).
SPC: Specially Processed Cereals
RTT: Method for measuring a standardized secretion response in rat small intestine, as published in SE 9000028-2 (publication number 466331) for measuring content of AF (ASP).
ARF: Acute respiratory failure
ARDS: Acute respiratory distress syndrome
IRDS: Infantile respiratory distress syndrome
BPD: Bronchopulmonary dysplasia
SIRS: Systemic inflammatory response syndrome
Sepsis: Infection with systemic manifestations of infection Definitions Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides, polypeptides, or oligopeptides. The terms "protein", "polypeptide", "oligopeptide" and "peptide" may be used interchangeably in the present context. Peptides can have very few amino acid residues, such as between 2-50 amino acid residues (aa).

A "pharmaceutical composition", in the present context, refers to a composition comprising a therapeutically active amount of an antisecretory factor (AF) protein, optionally in combination with a pharmaceutically active excipient, such as a carrier or a vehicle. Said pharmaceutical composition is formulated for the appropriate route of administration, which may vary depending on the condition of the patient, as well as on other factors, such as age or preferred choice. The pharmaceutical composition upon administration presents the active substance to the body of a human or an animal. Said pharmaceutical composition may be in the form of e.g. tablets, pills, lozenges, capsules, stool pills, gels, solutions, etc., but is not limited thereto.

The term "pharmaceutically active salt", refers to a salt of an antisecretory factor (AF) protein, peptide, or polypeptide, or a homologue and/or fragment thereof which may be any salt derived therefrom, based on so-called Hofmeister series. Other examples of pharmaceutically active salts comprise triflouroacetate, acetate and lysine chloride, the invention is not limited thereto.

The term "antisecretory" refers in the present context to inhibiting or decreasing secretion and/or fluid transfer. Hence, the term "antisecretory factor (AF) protein" refers to a family of proteins capable of inhibiting or decreasing or otherwise modulating fluid transfer as well as secretion in a body.

In the present context, "equivalent activity" is used interchangeably with the term "equivalent functional activity" and relates to the biological effect of the antisecretory factor (AF) protein, peptide, or polypeptide, or a homologue, derivative and/or fragment thereof, i.e. its capacity for improving therapy and/or treatment of ARF, for use in restoring and/or normalizing epithelial cell barrier function in pulmonary and/or systemic diseases. Standardized examples for testing and/or measuring such a capacity are well known in the field of the art. Examples are given in the experimental section of this application, such as in example 1. Further, the biological activity of an antisecretory factor (AF) protein, peptide, or polypeptide, or a homologue and/or fragment thereof according to the present invention can e.g. be tested in a standardized in vitro lung injury model, such as but not limited to in Caco-2 cells ATCC; [see e.g. V Nicolas & V Lievin-Le moal: Infection & Immunity 2015; 83:907-922]) wherein transcellular fluid-exchange and/or movement is measured.

In the present context, the term "equivalent activity" is used interchangeably with "analogous biological activity".

In the present context, the terms an "antisecretory factor protein", "antisecretory factor (AF) protein", "AF-protein", AF, or a homologue, or fragment thereof, may be used interchangeably with the term "antisecretory factors" or "antisecretory factor proteins" as defined in WO 97/08202, and refer to an antisecretory factor (AF) protein or a peptide or a homologue, and/or a fragment thereof having antisecretory and/or equivalent functional and/or analogue activity, or to a modification thereof not altering the function of the polypeptide. Hence, it is to be understood that an "antisecretory factor", "antisecretory factor protein", "antisecretory peptide", "antisecretory fragment", or an "antisecretory factor (AF) protein" in the present context, also can refer to a homologue or fragment thereof. These terms may all be used interchangeably in the context of the present invention. Furthermore, in the present context, the term "antisecretory factor" may be abbreviated "AF". Antisecretory factor (AF) protein in the present context refers to a protein with antisecretory properties as previously defined in WO97/08202 and WO 00/38535. Antisecretory factors have also been disclosed e.g. in WO 05/030246. Also intended by the term antisecretory factor are native antisecretory factors (NASPs) in egg yolk enriched and/or naturally rich in antisecretory factors as disclosed e.g. in SE 900028-2 and WO 00/38535 and in WO 2017/009004, as further described below. Additionally, alternative names have been used in the literature for the AF protein.

A "medical food", in the present context, refers to a food, a food supplement, or a food for special dietary use, which has been prepared with an antisecretory factor (AF) protein, or alternatively, has the capability to induce synthesis and/or activation of endogenous AF. Said food may be any suitable food, in fluid or solid form, such as a liquid or a powder, a bar, cereal, or any other suitable foodstuff. Examples of such matter may be found in WO 2017/009004, WO 0038535 and/or WO 91/09536.

A "nebulizer", in the present context, refers to a medical device that delivers liquid medication in the form of a mist to the airways.

The term "aerosol" in the present context refers to a gaseous suspension of fine solid or liquid particles.

In the present context, the term "adjuvant" is used to describe a pharmacological and/or immunological agent that modifies the effect of other agents. Adjuvants of in the present application enhance or optimize the recipient's use of the active substance administered, thus minimizing the necessary amount of said substance.

DETAILED DESCRIPTION OF THE INVENTION

The present invention relates to a new approach to counteract and/or prevent disturbed and/or impeded epithelial barrier functions for treating, ameliorating and/or preventing acute respiratory failure.

In particular, the present invention relates to the use of an antisecretory factor (AF) protein as shown in SEQ ID NO: 1 (AF) and/or a homologue and/or fragment thereof having equivalent activity and comprising an amino acid sequence as shown in SEQ ID NO: 2 (AF-6), and/or a pharmaceutically active salt thereof, and/or a food and/or food supplement, enriched in said antisecretory factor (AF) protein and/or homologue and/or fragment thereof, for restoring and/or normalizing epithelial barrier function for treating, ameliorating and/or preventing acute respiratory failure.

Epithelial Barrier Function

Diffusion barriers between blood and the alveolar air are constituted by the attenuated cytoplasm of pneumocytes, the basement membrane and the thin cytoplasm of a capillary endothelial cell.

Alveolar epithelium is made up of type I pneumocytes and type II pneumocytes, both of which rest on the basement membrane, which latter contribute to the interstitial tissue and contain a fraction of the interstitial fluid. A major function of the type II pneumocytes is to form and secrete surfactants Tight junctions of the epithelial cells can be disrupted, which leads to leaking of interstitial fluid, proteins and even cells to the alveoli, impairing respiration.

In acute respiratory failure, the epithelial barrier function of the lungs is impaired, hence generating an increased capillary permeability, leading to accumulation of fluid inside the alveoli. BPD, ARDS and IRDS are characterized by damage of the capillary endothelium and alveolar epithelium in association with impaired fluid removal from alveolar space and the accumulation of protein-rich fluid inside the alveoli.

The present invention for the first time describes the use of AF for restoring and/or normalizing epithelial cell barriers, thus effectively restoring and/or normalizing epithelial barrier function in patients suffering from acute respiratory failure, such as, but not limited to BPD, IRDS and/or ARDS, acute ARDS, severe ARDS, acute pulmonary edema and interstitial pulmonary edema.

As is shown in example 1, adult pigs with experimentally induced ARDS who were treated with intravenous infusion (iv) of the peptide AF-16, showed significantly reduced deleterious accumulation of fluid in alveoli and in the interstitial tissue (FIG. 3).

Furthermore, the beneficial effects were demonstrable within an hour and significantly lasted at least four hours.

Example 1 further demonstrates that AF-16 treatment reduced the structural abnormalities caused by the induced traumatic lung injury as compared to that documented for vehicle treated reference animals and that no adverse side effects could be demonstrated with regard to cardiovascular parameters, including blood pressure and heart rates.

Available results solidly indicate that AF-16 treatment has beneficial effects, which are statistically significant, on cardiac output in acute respiratory failure (FIG. 4).

The present invention therefore relates primarily both to treatments of the respiratory and the cardiovascular system.

In the respiratory system, it is of outmost importance that the breathed air is separated from the blood and interstitial fluid by tissue with a thickness in the range of tenths of micrometers to enable adequate uptake and exchange of oxygen and carbon dioxide. Only minimal amounts of fluid are allowed for proper normal, i.e. healthy, function of the respiratory tract including the lung alveoli. A large number of adverse medical conditions are therefore associated with deleteriously increased amounts of fluid in the alveoli impairing the respiration and eventually causing suffocation and/or drowning, either cardiogenic (e.g. due to heart infarct and other cardiomyopathies, severe hypertonia, acute decompensated heart failure), or non-cardiogenic (e.g. ARF, lung trauma, ARDS, IRDS, BPD, inhalation injury, sepsis, pneumonia, fluid overload, drowning, kidney diseases, liver disorders, neurogenic conditions such as brain hemorrhages, stroke, brain trauma).

Leakage and accumulation of fluid to the alveoli hamper the breathing and oxygenation and further increase the load on the heart due to disturbed circulation and accumulation of blood in the lungs, associated with severe morbidity and high mortality. Extended hypoxia and hypercapnia frequently result in persistent neuropsychiatric adverse symptoms and neurological functional deficits in surviving patients. Thus, long-term sequel may seriously impair the life quality and reduce the length of life. Presently available treatment-recommendations are mainly symptomatic and the treatments do only to a limited extent reduce the dangerous accumulation of fluid, debris and inflammatory cells in the alveoli and respiratory tract.

The antisecretory factor (AF) protein, peptide, derivative, homologue, and/or fragment thereof, having equivalent functional activity, and/or a pharmaceutically active salt thereof, has been investigated with regards to beneficial effects on the pathological accumulation of fluid in the lung and in extra-pulmonary parts of the respiratory system at conditions specified above.

In general, the present invention relates to the surprising insight that antisecretory factor (AF) significantly counteracts the accumulation of fluid in the respiratory system (FIG. 3) and exerts beneficial effects on the cardiovascular system (FIG. 4). There are currently no known other pharmaceutical substances, which reduce the fluid accumulation in the respiratory system including in the critical lung alveoli.

The present invention thus relates to the surprising finding that AF can effectively regulate and/or normalize abnormal activity of said trans-cellular fluid transfer in perturbed and/or pathological cells, thereby effectively normalizing the function of the for life critically important epithelial barrier function of the affected tissue and/or organ.

Hence, the present invention relates to the use of antisecretory factor (AF) protein as shown in SEQ ID NO: 1 (AF) and/or a homologue and/or fragment thereof having equivalent activity and comprising an amino acid sequence as shown in SEQ ID NO: 2 (AF-6), and/or a pharmaceutically active salt thereof, and/or a food and/or food supplement, enriched and/or naturally rich in said antisecretory factor (AF) protein and/or homologue and/or fragment thereof, wherein epithelial and/or endothelial barrier function is restored and/or normalized by restoring and/or normalizing epithelial and/or endothelial cell barrier functions for treating and/or preventing acute respiratory failure.

The Antisecretory Factor

The antisecretory factor is a class of proteins that occurs naturally in the body. The human antisecretory factor AF protein is a 41 kDa protein, comprising 382-288 amino acids when isolated from the pituitary gland. The active site with regard to the beneficial effect on in restoring and/or normalizing epithelial cell barrier function according to the present invention can be localized to the protein in a region close to the N-terminal parts of the protein, in particular it can be localized to amino acids 1-163 of SEQ ID NO 1, more specifically to amino acid positions 35-50 on the antisecretory factor (AF) protein sequence. The biological effect of AF has been shown to be exerted by any peptide or polypeptide comprising at least 6 amino acids, corresponding to SEQ ID NO: 2 (AF-6), of said consensus sequence, or a modification thereof not altering the function of the polypeptide and/or peptide.

The present inventors have shown that the antisecretory factor is to some extent homologous with the protein S5a, and Rpn10, which constitutes a subunit of a constituent prevailing in all cells, the 26 S proteasome, more specifically in the 19 S/PA 700 cap. In the present invention, antisecretory factor (AF) proteins are defined as a family of homologue proteins having the same functional properties. Antisecretory factor is also similar to angiocidin, another protein isoform known to bind to thrombospondin-1 and associated with cancer progression.

Homologues and fragments of antisecretory factor (AF) proteins and/or peptides according to the present invention all have analogous biological activity. Homologues and fragments, in the present context, comprise at least 6 amino acids (as shown in SEQ ID NO: 2) corresponding to those of a naturally occurring antisecretory factor (AF) protein, which may be further modified by changing one or more amino acids in order to optimize the antisecretory factor's biological activity, without altering the essential function of the polypeptide and/or peptide.

The antisecretory factor fragments and/or derivatives according to the invention may comprise an N-terminal and/or a C-terminal protecting group. One example of an N-terminal protecting group includes acetyl. One example of a C-terminal protecting group includes amide.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of an antisecretory factor (AF) protein, peptide, homologue, derivative and/or fragment according to the invention, is also considered to be inside the scope of the present invention.

By proteins, homologues, peptides and/or fragments thereof having an amino acid sequence at least, for example 95% identical to a reference amino acid sequence, is intended that the amino acid sequence of e.g. the peptide is identical to the reference sequence, except that the amino acid sequence may include up to 5 point mutations per each 100 amino acids of the reference amino acid sequence. In other words, to obtain a polypeptide having an amino acid sequence at least 95% identical to a reference amino acid sequence, up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith Waterman) compare a subsequence in one sequence with a subsequence in a second sequence and find the combination of sub-sequences and the alignment of those sub-sequences, which yields the highest overall similarity score. Internal gaps, if allowed, are penalized. Local algorithms work well for comparing two multi domain proteins, which have a single domain, or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The antisecretory factor (AF) proteins or a peptide or a homologue and/or fragment thereof having equivalent activity as defined herein, can comprise 6 amino acids or more, such as 6-16 amino acids, such as 6, 7, 8, 9, 10, 11, 12, 13, 14, 15, 16, 17, 18, 19 or 20 amino acids or more. In other preferred embodiments the antisecretory factor consists of 42, 43, 45, 46, 51, 80, 128, 129 or 163 amino acids. In preferred embodiments the antisecretory factor (AF) protein, a homologue, peptide and/or fragment thereof, according to the present invention, consists of 6, 7, 8 or 16 amino acids.

The antisecretory factor (AF) protein, a homologue, peptide and/or fragment thereof, according to the present invention, can be produced in vivo or in vitro, e.g. be recombinantly, synthetically and/or chemically synthesized, and/or isolated from a naturally occurring source of antisecretory factors, such as from pig pituitary glands or bird's eggs. After production, the antisecretory factor (AF) protein, a homologue, peptide and/or fragment thereof, according to the present invention may be further processed, such as by chemical or enzymatic cleavage to smaller antisecretory active fragments or by modification of amino acids. It is presently not possible to obtain antisecretory factor (AF)-protein in pure form by purification. It is however possible to produce a biologically active antisecretory factor protein recombinantly or synthetically as previously disclosed in WO 97/08202 and WO 05/030246. WO 97/08202 also discloses the production of biologically active fragments of this protein of 7-80 amino acids.

The antisecretory factor (AF) protein, a homologue, peptide and/or fragment thereof, according to the present invention may further comprise an N-terminal and/or a C-terminal protecting group. One example of an N-terminal protecting group includes acetyl. One example of a C-terminal protecting group includes amide.

In a preferred embodiment of the present invention the antisecretory factor (AF) protein, a homologue, peptide and/or fragment thereof, according to the present invention is selected among SEQ ID NOs 1-6, i.e. VCHSKTRSN-PENNVGL (SEQ ID NO 3, in this context also called AF-16), IVCHSKTR (SEQ ID NO 5), VCHSKTR (SEQ ID NO 4), CHSKTR (SEQ ID NO 2), HSKTR (SEQ ID NO 6), or the amino acid sequence of an antisecretory factor (AF) protein according to SEQ ID NO 1, using the common one letter abbreviations for amino acids. They have previously been disclosed in e.g. WO 05/030246. As specified in the accompanying sequence listing, some of the amino acids in the above-specified sequences may be replaced by other amino acids. In the following in this paragraph, the position of a particular amino acid in a particular amino acid sequence is calculated from the left, denoting the most N-terminal amino acid as being in position 1 in that particular sequence. Any amino acid substitution(s) as specified below may be performed independently of any other amino acid substitution(s) in that sequence.

In SEQ ID NO 3, the C in position 2 may be replaced by S, H in position 3 may be replaced with R or K, S in position 4 may be replaced with L, and/or T in position 6 may be replaced with A. In SEQ ID NO 5, C in position 3 may be replaced by S, H in position 4 may be replaced by R or K, S in position 5 may be replaced by L, and/or T in position 7 may be replaced by A. In SEQ ID NO 4, C in position 2 may be replaced by S, H in position 3 may be replaced by R or K, S in position 4 may be replaced by L, and/or T in position 6 may be replaced by A. In SEQ ID NO 2, C in position 1 may be replaced by S, H in position 2 may be replaced by R or K, S in position 3 may be replaced by L, and/or T in position 5 may be replaced by A. In SEQ ID NO 6, H in position 1 may be replaced by R or K, S in position 2 may be replaced by L, and/or T in position 4 may be replaced by A.

Also intended by the present invention is the combination of two or more of any of the fragments/peptides according to SEQ ID NO: 1-6.

Specific antisecretory factor (AF) proteins or peptides to be used according to and/or which are included by the present invention are selected from the group consisting of an antisecretory factor (AF) protein comprising an amino acid sequence as shown in SEQ ID NO: 1, an antisecretory factor (AF) protein which comprises an amino acid sequence as shown in SEQ ID NO: 2, an antisecretory factor (AF) protein which comprises an amino acid sequence as shown in SEQ ID NO: 3, an antisecretory factor (AF) protein which comprises an amino acid sequence as shown in SEQ ID NO: 4 and an antisecretory factor (AF) protein which comprises an amino acid sequence as shown in SEQ ID NO: 5.

Furthermore, in yet another embodiment, the invention pertains to the use of an antisecretory factor (AF) protein which is a protein with an amino acid sequence as shown in SEQ ID NO:1, or a homologue, derivative and/or fragment thereof comprising amino acids 37-42 of SEQ ID NO:1.

In yet another embodiment, the invention relates to the use of a pharmaceutical composition as disclosed herein, which comprises two or more antisecretory factor (AF) proteins selected from the proteins as disclosed in SEQ ID NO: 1-6, and SEQ ID NO 1 or a homologue, derivative and/or fragment thereof comprising amino acids 37-42 of SEQ ID NO 1, or a sequence as disclosed by the general formulae described herein. Said sequences are all equally preferred to be used in the present invention.

WO 00/038535 discloses food products, enriched and/or naturally rich in antisecretory factor (AF) proteins as such, which are examples for suitable food, foodstuff and/or food supplements for use in the present context. Another example for use in the present context is an egg yolk comprising at least 0.05 ng/ml antisecretory factor (AF) protein fragment with an amino acid sequence as disclosed in SEQ ID NO: 3 and/or in SEQ ID NO: 4, such as is disclosed in WO 2017/009004.

Pharmaceutical Composition

In one embodiment of the present invention, the pharmaceutical composition according to the invention further comprises a pharmaceutically acceptable excipient. The choice of pharmaceutically acceptable excipient and their optimum concentration for use according to the present invention can readily be determined by the skilled person by experimentation. Pharmaceutically acceptable excipients for use according to the present invention include solvents, buffering agents, preservatives, chelating agents, antioxidants, and stabilizers, emulsifying agents, suspending agents and/or diluents. The pharmaceutical compositions of the invention may be formulated according to conventional pharmaceutical practice, e.g. according to "Remington: The science and practice of pharmacy", 21st edition, ISBN 0-7817-4673-6 or "Encyclopedia of pharmaceutical technology", 2nd edition, ed. Swarbrick J., ISBN: 0-8247-2152-7.

A pharmaceutically acceptable excipient is a substance that is substantially harmless to the individual to which the composition is to be administered. Such an excipient normally fulfills the requirements given by the national health authorities. Official pharmacopoeias such as e.g. the British Pharmacopoeia, the United States of America Pharmacopoeia and The European Pharmacopoeia set standards for pharmaceutically acceptable excipients.

The following is a review of relevant compositions for optional use in a pharmaceutical composition according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient. It should be emphasized that the invention is not limited to the use of the compositions mentioned in the following.

Parenteral Compositions:

For systemic application, the compositions according to the invention may contain conventional non-toxic pharmaceutically acceptable carriers and excipients, including micro spheres and liposomes.

The compositions for use according to the invention may include all kinds of solid, semi-solid and fluid compositions.

The pharmaceutically acceptable excipients may include solvents, buffering agents, preservatives, chelating agents, antioxidants, and stabilizers, emulsifying agents, suspending agents and/or diluents. Examples of the different agents are given bellow.

Example of Various Agents:

Examples of solvents include but are not limited to water, alcohols, blood, plasma, cerebrospinal fluid, ascites fluid and lymph fluid.

Examples of buffering agents include but are not limited to citric acid, acetic acid, tartaric acid, lactic acid, hydrogen phosphoric acid, bicarbonates, phosphates, diethylamide, etc.

Examples of chelating agents include but are not limited to EDTA and citric acid.

Examples of antioxidants include but are not limited to butylated hydroxyl anisole (BHA), ascorbic acid and derivatives thereof, tocopherol and derivatives thereof, cysteine, and mixtures thereof.

Examples of diluents and disintegrating agents include but are not limited to lactose, saccharose, emdex, calcium phosphates, calcium carbonate, calcium sulphate, mannitol, starches and microcrystalline cellulose.

Examples of binding agents include but are not limited to saccharose, sorbitol, gum acacia, sodium alginate, gelatine, chitosan, starches, cellulose, carboxymethylcellulose, methylcellulose, hydroxypropylcellulose, polyvinylpyrrolidone and polyetyleneglycol.

The pharmaceutical composition according to the invention is in one context administrated locally or via intravenous infusion or infusion in a central vessel or organ-related vessel or duct, or via intramuscular or subcutaneous injection into the patient or via buccal, pulmonary, nasal, cutaneous or oral routes. Furthermore, it is also possible to administer the pharmaceutical composition through a surgically inserted shunt into the brain parenchyma, or a cerebral ventricle or spaces in or around the nervous system of the patient.

In one embodiment, the pharmaceutical composition for use according to the present invention is formulated for intraocular, local, intranasal, oral, cutaneous, subcutaneous and/or systemic administration. The chosen route of administration will vary depending on the condition of the patient to be treated and the patient's age and gender etc. In a preferred embodiment, the composition of the invention is administrated by application as a suspension or, even more preferably, a powder for inhalation with a spray, aerosol, inhaler or nebulizer nasally and/or to the respiratory tract.

The administration of a powder comprising antisecretory factors has the additional advantages in terms of stability and dosage. A pharmaceutical composition according to the invention can also be topically applied, ocularly, nasally, orally, cutaneously, subcutaneously and/or systemically administered via blood vessels. In a preferred embodiment, the pharmaceutical composition is formulated for intravenous, intramuscular, local, oral or nasal administration. Typically, when used for topical application to the eye, the applied concentration in the composition of the invention is from 1 µg to 100 mg per application, preferably 50-5000 µg, either as a single dose per day or repeated several times per day (multiple doses), but is not limited thereto.

Systemically administrated to the blood, the dose is within the range of 0.1 µg to 10 mg per application and kg body weight, such as 0.1 µg to 100 mg per application and kg body weight, preferably 1-5000, such as 1-10000 µg/kg body weight. When egg yolk enriched and/or naturally rich in antisecretory factors is used according to the present invention, this formulation is preferably administered orally, by a tube and/or by feeding tube.

In one embodiment of the invention, said pharmaceutical composition further comprises a pharmaceutically acceptable excipient. Such an excipient may be any preferable excipient chosen to be appropriate for the specific purpose. Examples of excipients are disclosed herein.

Salovum®

The present invention further relates to egg yolk enriched and/or naturally rich in antisecretory factor (AF) proteins, presently marketed under the trademark Salovum® and to its use for preparation of food and/or food supplement enriched and/or naturally rich in said antisecretory factor (AF) protein and/or homologue and/or fragment thereof for restoring and/or normalizing epithelial barrier function in pathogenesis of acute respiratory failure, such as but not limited to the treatment of patients with abnormal accumulation of fluid in the lung alveoli and bronchioles, acute respiratory failure, ARDS (acute respiratory distress syndrome), IRDS (infant respiratory distress syndrome), SIRS (systemic inflammatory response syndrome), other severe systemic inflammatory conditions and/or cardiovascular lung disorder.

The present invention further relates to a food and/or food supplement, enriched and/or naturally rich in said antisecretory factor (AF) protein and/or homologue and/or fragment thereof, wherein the food and/or food supplement, enriched and/or naturally rich in the antisecretory factor (AF) protein and/or homologue and/or fragment thereof is provided as egg yolk enriched and/or naturally rich in antisecretory factors, such as egg yolk enriched in naturally occurring antisecretory factors (NASPs) as disclosed in WO 00/038535 for restoring and/or normalizing epithelial barrier function in pathogenesis of acute respiratory failure (ARF), such as but not limited to the treatment of patients with abnormal accumulation of fluid in the lung alveoli and bronchioles, BPD, ARDS, IRDS, sepsis, SIRS (systemic inflammatory response syndrome), other severe systemic inflammatory conditions and/or cardiovascular lung disorder.

The present invention further relates to a food and/or food supplement, enriched and/or naturally rich in a antisecretory factor (AF) protein and/or homologue and/or fragment thereof which is provided as egg yolk comprising at least 0.05 ng/ml antisecretory factor (AF) protein fragment with an amino acid sequence as disclosed in SEQ ID NO 3 and/or in SEQ ID NO 4, such as disclosed in WO 2017/009004, for restoring and/or normalizing epithelial barrier function in pathogenesis of acute respiratory failure (ARF), such as but not limited to the treatment of patients with abnormal accumulation of fluid in the lung alveoli and bronchioles, BPD, ARDS, IRDS, sepsis, SIRS (systemic inflammatory response syndrome), other severe systemic inflammatory conditions and/or cardiovascular lung disorder.

Egg yolk compositions, enriched and/or naturally rich in antisecretory factor (AF) protein and/or homologues and/or fragments thereof, for a use as described herein and as by reference incorporated herein, disclosed e.g. in WO 00/038535 or WO 2017/009004, can be provided as food, food supplements, pharmaceutical compositions and/or as medical food.

Method of Treatment

The present invention further relates to the treatment of acute respiratory failure (ARF), such as but not limited to the treatment of patients with abnormal accumulation of fluid in the lung alveoli and bronchioles, BPD, ARDS, IRDS, sepsis, SIRS, and/or cardiovascular lung disorder, by administering to a patient in need thereof an antisecretory factor (AF) protein and/or a homologue and/or fragment thereof and/or a pharmaceutically active salt thereof, and/or a food and/or food supplement, enriched and/or naturally rich in said antisecretory factor (AF) protein and/or homologue and/or fragment, in a pharmaceutical composition and/or medical food which is formulated for administration systemically to the blood at a dose of 0.1 µg to 100 mg per application and kg body weight, preferably 1-10000 µg per application and kg body weight and, wherein said administration is performed either as a single dose or as multiple daily applications.

The present invention further relates to a method for treatment, prevention and/or prophylactic treatment of acute respiratory failure (ARF), such as but not limited to the treatment of patients with abnormal accumulation of fluid in the lung alveoli and bronchioles, BPD, ARDS, IRDS, sepsis, SIRS, and/or cardiovascular lung disorder, wherein an antisecretory factor (AF) protein as shown in SEQ ID NO: 1 (AF) and/or a homologue and/or fragment thereof comprising an amino acid sequence as shown in SEQ ID NO: 2 (AF-6), and/or a pharmaceutically active salt thereof, and/or a food and/or food supplement, enriched and/or naturally rich in said antisecretory factor (AF) protein and/or homologue and/or fragment thereof, is administered to a mammal in need thereof in an amount sufficient for restoring and/or normalizing epithelial cell-barrier function.

The present invention further relates to a method for treatment, prevention and/or prophylactic treatment of acute respiratory failure (ARF), such as but not limited to the treatment of patients with abnormal accumulation of fluid in the lung alveoli and bronchioles, BPD, ARDS, IRDS, sepsis, SIRS, and/or cardiovascular lung disorder.

EXPERIMENTAL SECTION

Example 1

ARDS Model Based on Respiratory Tract Lavage and Injurious Ventilation

Background

The aim of the experiment was to elucidate the effects of the peptide AF-16 administered to adult pigs with experimentally induced ARDS.

Experimental Setup

After ethical approval, 3 months old pigs (body weight 30-35 kg), in all 12, were purchased from a local farm and 2 pigs on 6 occasions brought to the laboratory in the morning on the day for the experiment. Two pigs were used in parallel, one randomly assigned to be treated with AF-16 while the other one instead had a vehicle, sterile saline. Upon arrival, the pigs were sedated and thereafter kept fully anaesthetized during the entire experiment until termination late the same day. Tracheostomy was performed and mechanical ventilation performed with a ventilator. This setup is visualized in FIG. 1. Tubes positioned in arteries, veins and via a vein also in the right heart. Equipment was implanted to enable the use of PiCCO instrument (Pulse index, Continuous Cardiac Output=PiCCO) in order to enable exact determination of the total blood volume in the lungs, extra-vascular lung water (EVLW) and cardiac function parameters. Blood pressure transducers were inserted in the pulmonary artery and in a central artery. Arterial blood gasses and additional blood parameters were checked at regular intervals. Oximetry was used to determine hemoglobin oxygen saturation in arterial blood. The core body temperature was kept automatically at desired normal level. EKG was recorded. All instruments were connected to an intensive care control panel and to a computer to enable continuous documentation and retrieval of saved data. Fluid infusion was given intravenously (iv) under strict control to avoid overhydration. The stated precautions and treatments kept the animal in good condition.

After stabilization, lung injury was induced by flushing saline having a controlled temperature in the bronchial tree, thereby inducing surfactant depletion and a collapse prone-lung. This was followed by one hour of injurious ventilation (i.e., ventilation with high inspiratory and low end-expiratory airway pressures) producing traumatic lung damage at the alveolar level. The parameters regarding the mechanical ventilation were regulated with the aid of a ventilator. Within one hour, increasing volumes of fluid accumulated in the alveoli, which even at an early stage severely reduced the uptake of oxygen and hampered the efflux of carbon dioxide.

Treatment with the peptide AF-16 or the vehicle started after the induction of the lung injury (i.e., after the injurious ventilation). During 10 minutes AF-16 dissolved in saline was infused intravenously in one of the two pigs taking part in each experiment and day. The second pig had concomitantly the vehicle infused. It was not known to the laboratory people taking part in the experiment which animal got the drug to be tested and which one had had the vehicle, and the code was not made available until after all experiments. The PiCCO values were determined once every hour for up to 4 hours after the infusion of the test substance. Eventually the experiments were terminated, the animals were euthanized and autopsy performed.

The PiCCO system was used to measure with high accuracy the extra-vascular lung water (EVLW) that is the water present in the lung alveoli and in the interstitial tissue, with the pulmonary blood volume excluded. Presence of fluid in the alveolar lumen reduces the volume of air in each alveolus and further increases the distance and thereby hampers and even eliminates the exchange of oxygen/carbon dioxide between respiratory air and the blood in the lung capillaries, resulting in, particularly, hypoxemia. The edema per se, will also augment the ventilator induced lung injury and inflammation (the ventilator will by the positive pressure delivered to the lungs induce lung injuries) and initiate a vicious circle that increases inflammation and the likelihood of developing sepsis. This inflammatory reaction will then spread systematically and result in cell death in multiple organs and tissues. In fact, the most common cause of death in ARDS is multiple organ failure due to this reason.
Results
(See FIG. 3)

The EVLW volume was at the start of the experiment about 330 ml (mean for 6 pigs treated with AF-16 and 6 pigs having had the vehicle) as determined by the PiCCO system. The mean body weight for the pigs was about 35 kg.

Induction of lung damage by flushing the respiratory tract with tempered saline resulted after 1 hour in EVLW increasing to 500-520 ml as determined for 6 pigs aimed to be treated with AF-16 and 6 pigs having only had the vehicle.

The infusion of 2 mg/kg body weight of AF-16 resulted in 1 hour in a reduction of the decreased EVLW, being reduced to 460 ml, which is statistically significantly different from the 510 mL EVLW demonstrable for the vehicle treated 6 pigs.

At 2 hours after the AF-16 infusion, the mean EVLW for the 6 pigs treated with AF-16 was reduced to 430 ml, significantly differing from the 505 mL measured for the vehicle group.

At 3 hours after the treatment with AF-16, the 6 pigs had an even lower EVLW volume, 420 ml, which is significantly differing from the 500 mL measured for the vehicle group.

After 4 hours the EVLW content, 400 ml, in the AF-16 treated pigs, was still significantly different from that of the vehicle treated ones, 480 ml.

Photos of the pigs' lungs were taken at autopsy 5 hours after the induction of lung damage and after being treated during 4 hours with either a single infusion of AF-16 or of the vehicle, saline. The photos are seen in FIG. 2. The lungs treated with AF-16 demonstrate close to normal appearance with minimal bleedings at both the left and right lung lobes. In contrast, the lungs from the 6 pigs treated with the vehicle show extensive atelectasis and hemorrhages discoloring the tissue to appear dark bilaterally. Only limited areas of the upper parts of the vehicle treated lungs are of normal appearance, indicating restricted functional capacity of the vehicle lungs. The vehicle treated lungs became heavy and swollen, resulting in that pressure hemorrhagic patterns from the thoracic rib cage became visible (FIG. 3).

Further, the cardiac output (CO) remained almost at the same level as the initial baseline values in the AF-16 treated pigs with ALI (FIG. 4). In contrast, vehicle infusion turned the CO to remain at a significantly lower level. The increased CO could be interpreted be due to a normalized pulmonary vascular resistance due to less pulmonary edema. In this model, pulmonary edema results in compressed alveolar vessels and increased pulmonary vasoconstriction increasing the pulmonary vascular resistance and impairing the flow through the lungs and thus CO.

CONCLUSIONS

The main conclusion is that intravenous infusion of the peptide AF-16 significantly reduced the deleterious accumulation of fluid in alveoli and in the interstitial tissue in experimentally injured lungs and that the beneficial effects were demonstrable within an hour and lasted at least three to four hours.

No adverse side effects could be demonstrated with regard to cardiovascular parameters, including blood pressure and heart rates.

Available results indicated beneficial effects of AF-16 on cardiac output, i.e. improved heart function. This observation is important, since right heart failure is not uncommon in acute lung diseases.

REFERENCES

1. Lange, S., and Lönnroth, I. 2001. The antisecretory factor: synthesis, anatomical and cellular distribution, and biological action in experimental and clinical studies. *Int. Rev. Cytol.* 210, 39-75.
2. H.-A. Hansson, M. Al-Olama, E. Jennische, K. Gatzinsky and S. Lange (2012). The peptide AF-16 and the AF protein counteract intracranial hypertension. Acta Neurochir. Suppl. 114, 377-382.
3. Remington: The science and practice of pharmacy", 21st edition, ISBN 0-7817-4673-6 or "Encyclopedia of pharmaceutical technology", 2nd edition, ed. Swarbrick J., ISBN: 0-8247-2152-7.
4. WO 97/08202;
5. WO 05/030246
6. WO 97/08202
7. WO 97/08202
8. WO 98/21978
9. WO 00/038535.
10. WO 05/030246
11. WO 07/126364
12. WO 07/126363
13. WO 07/126365
14. WO 2010/093324
15. Sakka S. G. Extravascular lung water in ARDS patients. Minerva Anestesiol. 2013; 79: 274-284.
16. Singer M, Deutschman C S, Seymore C W et al. The third international consensus definitions for sepsis and septic shock [Sepsis-3]. JAMA 2016; 315:801-810
17. Calfee et al., Trauma-associated lung injury differs clinically and biologically from acute lung injury due to other clinical disorders, Crit Care Med. 2009.
18. Claesson J, Freundlich M, Gunnarsson I, Laake J H, Möller M H, et al. Scandinavian clinical practice guideline on fluid and drug therapy in adults with acute respiratory distress syndrome. Acta Anaesth Scand 2016; 60: 697-709.

19. Huppert L A and Matthay M A. Alveolar Fluid Clearance in Pathologically Relevant Conditions: In Vitro and In Vivo Models of Acute Respiratory Distress Syndrome.

Front. Immunol. 2017; 8:371. doi: 10.3389/fimmu.2017.00371

20. Altschul, S. F., Gish, W., Miller, W., Myers, E. w., Lipman, D. J. Basic local alignment search tool. Journal of Molecular Biology 1990; 215/3: 403-410

The invention claimed is:

1. A method for treatment and/or prophylactic treatment of acute respiratory failure (ARF) in a mammal, comprising administering to a mammal in need thereof an antisecretory factor (AF) protein as shown in SEQ ID NO: 1 and/or a homologue and/or fragment thereof comprising an amino acid sequence as shown in SEQ ID NO: 2, and/or a pharmaceutically active salt thereof, in an amount sufficient for restoring epithelial barrier function.

2. A method for treatment and/or prophylactic treatment-according to claim 1, for treating acute respiratory failure (ARF) in a human patient with accumulation of fluid in the lung alveoli and/or bronchioles selected from the list of patients suffering from bronchopulmonary dysplasia (BPD), acute respiratory distress syndrome (ARDS), infantile respiratory distress syndrome (IRDS), sepsis, systemic inflammatory response syndrome (SIRS), acute pulmonary edema, pneumonia, interstitial pulmonary edema and cardiovascular lung disorder.

3. A method for treatment and/or prophylactic treatment-according to claim 1, wherein ARDS is selected from the group consisting of acute ARDS and severe ARDS.

4. A method for treatment and/or prophylactic treatment-according to claim 1, wherein said antisecretory factor (AF) protein and/or a homologue and/or fragment thereof and/or a pharmaceutically active salt thereof, is formulated in a pharmaceutical composition.

5. A method for treatment and/or prophylactic treatment according to claim 4, wherein said antisecretory factor (AF) protein and/or a homologue and/or fragment thereof and/or a pharmaceutically active salt thereof, is formulated in a pharmaceutical composition comprising at least two or more antisecretory factor (AF) proteins and/or homologues and/or fragments thereof and/or pharmaceutically active salts thereof and a pharmaceutically acceptable excipient.

6. A method for treatment and/or prophylactic treatment according to claim 4, wherein said pharmaceutical composition is formulated for intraocular, intranasal, oral, local, subcutaneous and/or systemic administration.

7. A method for treatment and/or prophylactic treatment according to claim 4, wherein said pharmaceutical composition is formulated for administration as a spray, aerosol, inhaler and/or by a nebulizer.

8. A method for treatment and/or prophylactic treatment according to claim 4, wherein the pharmaceutical composition is formulated for administration systemically to the blood at a dose of 0.1 μg to 100 mg per kg body weight and, wherein said administration is performed either as a single dose or as multiple daily applications.

9. A method for treatment and/or prophylactic treatment according to claim 8, wherein the pharmaceutical composition is formulated for administration systemically to the blood at a dose of 1-10000 μg per kg body weight.

10. A method for treatment and/or prophylactic treatment according to claim 1, wherein the antisecretory factor (AF) protein as shown in SEQ ID NO: 1 and/or a homologue and/or fragment thereof comprising an amino acid sequence as shown in SEQ ID NO: 2 is provided in a food and/or food supplement.

11. A method for treatment and/or prophylactic treatment according to claim 10, wherein the food and/or food supplement is an egg yolk.

12. A method for treatment and/or prophylactic treatment according to claim 11, wherein said egg yolk comprises at least 0.05 ng/ml antisecretory factor (AF) protein fragment with an amino acid sequence as disclosed in SEQ ID NO: 3 and/or SEQ ID NO: 4.

\* \* \* \* \*

```
                          SEQUENCE LISTING

<160> NUMBER OF SEQ ID NOS: 6

<210> SEQ ID NO 1
<211> LENGTH: 382
<212> TYPE: PRT
<213> ORGANISM: Homo sapiens

<400> SEQUENCE: 1

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
            115                 120                 125

Lys Arg Leu Lys Lys Glu Lys Val Asn Val Asp Ile Ile Asn Phe Gly
        130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
            195                 200                 205

Asp Pro Ser Ala Asp Pro Glu Leu Ala Leu Ala Leu Arg Val Ser Met
    210                 215                 220

Glu Glu Gln Arg His Ala Gly Gly Gly Ala Arg Arg Ala Ala Arg Ala
225                 230                 235                 240

Ser Ala Ala Glu Ala Gly Ile Ala Thr Thr Gly Thr Glu Asp Ser Asp
            245                 250                 255

Asp Ala Leu Leu Lys Met Thr Ile Ser Gln Gln Glu Phe Gly Arg Thr
            260                 265                 270

Gly Leu Pro Asp Leu Ser Ser Met Thr Glu Glu Glu Gln Ile Ala Tyr
        275                 280                 285

Ala Met Gln Met Ser Leu Gln Gly Ala Glu Phe Gly Gln Ala Glu Ser
    290                 295                 300

Ala Asp Ile Asp Ala Ser Ser Ala Met Asp Thr Ser Glu Pro Ala Lys
```

```
305                 310                 315                 320

Glu Glu Asp Asp Tyr Asp Val Met Gln Asp Pro Glu Phe Leu Gln Ser
                325                 330                 335

Val Leu Glu Asn Leu Pro Gly Val Asp Pro Asn Asn Glu Ala Ile Arg
                340                 345                 350

Asn Ala Met Gly Ser Leu Pro Pro Arg Pro Pro Arg Thr Ala Arg Arg
            355                 360                 365

Thr Arg Arg Arg Lys Thr Arg Ser Glu Thr Gly Gly Lys Gly
        370                 375                 380

<210> SEQ ID NO 2
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: VARIANT
<222> LOCATION: 5
<223> OTHER INFORMATION: Thr or Ala
<221> NAME/KEY: VARIANT
<222> LOCATION: 2
<223> OTHER INFORMATION: His or Arg or Lys
<221> NAME/KEY: VARIANT
<222> LOCATION: 3
<223> OTHER INFORMATION: Ser or Leu
<221> NAME/KEY: VARIANT
<222> LOCATION: 1
<223> OTHER INFORMATION: Cys or Ser

<400> SEQUENCE: 2

Xaa Xaa Xaa Lys Xaa Arg
1               5

<210> SEQ ID NO 3
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: VARIANT
<222> LOCATION: 6
<223> OTHER INFORMATION: Thr or Ala
<221> NAME/KEY: VARIANT
<222> LOCATION: 3
<223> OTHER INFORMATION: His or Arg or Lys
<221> NAME/KEY: VARIANT
<222> LOCATION: 4
<223> OTHER INFORMATION: Ser or Leu
<221> NAME/KEY: VARIANT
<222> LOCATION: 2
<223> OTHER INFORMATION: Cys or Ser

<400> SEQUENCE: 3

Val Xaa Xaa Xaa Lys Xaa Arg Ser Asn Pro Glu Asn Asn Val Gly Leu
1               5                   10                  15

<210> SEQ ID NO 4
<211> LENGTH: 7
<212> TYPE: PRT
<213> ORGANISM: Artificial sequence
<220> FEATURE:
<223> OTHER INFORMATION: synthetic
<220> FEATURE:
<221> NAME/KEY: VARIANT
<222> LOCATION: 6
<223> OTHER INFORMATION: Arg or Ala
<221> NAME/KEY: VARIANT
<222> LOCATION: 3
```

-continued

```
<223> OTHER INFORMATION: His or Arg or Lys
<221> NAME/KEY: VARIANT
<222> LOCATION: 4
<223> OTHER INFORMATION: Ser or Leu
<221> NAME/KEY: VARIANT
<222> LOCATION: 2
<223> OTHER INFORMATION: Cys or Ser

<400> SEQUENCE: 4

Val Xaa Xaa Xaa Lys Thr Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 7
<223> OTHER INFORMATION: Thr or Ala
<221> NAME/KEY: VARIANT
<222> LOCATION: 4
<223> OTHER INFORMATION: His or Arg or Lys
<221> NAME/KEY: VARIANT
<222> LOCATION: 5
<223> OTHER INFORMATION: Ser or Leu
<221> NAME/KEY: VARIANT
<222> LOCATION: 3
<223> OTHER INFORMATION: Cys or Ser

<400> SEQUENCE: 5

Ile Val Xaa Xaa Xaa Lys Xaa Arg
1               5

<210> SEQ ID NO 6
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: VARIANT
<222> LOCATION: 1
<223> OTHER INFORMATION: His or Arg or Lys
<221> NAME/KEY: VARIANT
<222> LOCATION: 2
<223> OTHER INFORMATION: Ser or Leu
<221> NAME/KEY: VARIANT
<222> LOCATION: 4
<223> OTHER INFORMATION: Thr or Ala

<400> SEQUENCE: 6

Xaa Xaa Lys Xaa Arg
1               5
```